United States Patent
Miller et al.

(10) Patent No.: US 7,885,703 B2
(45) Date of Patent: Feb. 8, 2011

(54) SYSTEM AND METHOD FOR SCANNING A PATIENT

(75) Inventors: Michael Ronald Miller, Waukesha, WI (US); Phil E. Pearson, Hartland, WI (US); Jay Burns, IV, Waukegan, IL (US)

(73) Assignee: General Electric Company, Schenectady, NY (US)

( * ) Notice: Subject to any disclaimer, the term of this patent is extended or adjusted under 35 U.S.C. 154(b) by 980 days.

(21) Appl. No.: 10/950,870

(22) Filed: Sep. 27, 2004

(65) Prior Publication Data

US 2006/0074286 A1 Apr. 6, 2006

(51) Int. Cl.
*A61B 5/05* (2006.01)
(52) U.S. Cl. .............. 600/418; 600/407; 600/410; 348/53; 348/61
(58) Field of Classification Search ........... 348/53, 348/61; 600/410, 418, 407
See application file for complete search history.

(56) References Cited

U.S. PATENT DOCUMENTS

| | | | | |
|---|---|---|---|---|
| 4,593,183 A | * | 6/1986 | Fukatsu | 235/379 |
| 5,363,844 A | * | 11/1994 | Riederer et al. | 600/413 |
| 5,414,459 A | * | 5/1995 | Bullwinkel | 348/53 |
| 5,681,259 A | | 10/1997 | August | |
| 5,706,070 A | * | 1/1998 | Reich et al. | 351/201 |
| 5,864,331 A | * | 1/1999 | Anand et al. | 345/656 |
| 6,081,611 A | | 6/2000 | Linford et al. | |
| 6,774,929 B1 | * | 8/2004 | Kopp | 348/61 |
| 2003/0026464 A1 | * | 2/2003 | Kamiyama et al. | 382/128 |
| 2003/0046186 A1 | * | 3/2003 | Wren | 705/27 |
| 2004/0082847 A1 | * | 4/2004 | McDermott | 600/410 |
| 2004/0092809 A1 | * | 5/2004 | DeCharms | 600/410 |
| 2005/0165626 A1 | * | 7/2005 | Karpf | 705/3 |

* cited by examiner

*Primary Examiner*—Long V Le
*Assistant Examiner*—Ellsworth Weatherby
(74) *Attorney, Agent, or Firm*—Armstrong Teasdale LLP

(57) ABSTRACT

Systems and methods for using a patient display is described. The described system includes a medical imaging system. The medical imaging system includes a gantry, a patient display, and a computer. The gantry at least partially circumscribes a patient viewing area. The patient display is viewable from the patient viewing area. The patient display is communicatively coupled to the computer. The computer is programmed to receive scan protocol instructions and control the patient display according to the predetermined scan protocol. It is further programmed to prompt the patient, using the patient display, to perform a bodily action that facilitates the scan and to provide the patient with at least one of entertainment and distraction using the patient display.

44 Claims, 4 Drawing Sheets

SYSTEM AND METHOD FOR SCANNING A PATIENT

BACKGROUND OF THE INVENTION

This invention relates generally to medical imaging systems, and more particularly, to a display viewed by patients during scanning.

At least some known scan procedures require patients to perform certain actions during scanning. For example, in Computed Tomography (CT) the patients may be required to regulate their breathing patterns during scanning procedures. Further, the patients may be required to hold their breath during a quick scan. Therefore, to facilitate scanning it may be required to prompt a patient to perform a bodily action at a predetermined time. A technician can prompt the patient. However, there may be a problem if the technician and the patient are not well versed in a common language.

Further, cooperation from patients may be required to reduce movement artifacts. These can be reduced if the patient remains still during scanning. The technician verbally prompting a patient to remain still may, however, present language problems as mentioned earlier.

Another problem may be that the patients do not understand, the need to remain still during the scanning procedure. Furthermore, the imaging procedure and machinery may agitate the pateint. A number of patients may also experience anxiety and uneasiness during scanning. This may further reduce the patients' willingness to cooperate.

If the patients are pacified, it may lead to an improved experience for the patient as well as make them more cooperative, thereby, improving the outcome of the scanning procedure. Such a device to pacify the patients, and to prompt them in a way that the patients comprehend and follow, would work better if it were non-invasive. This is because physical restraints may exacerbate the anxiety of the patients and escalate the related problems. A physical restraint may also be a hindrance in the proper scanning or acquiring other data such as measuring respiration for the purposes of respiratory gating during CT scans.

BRIEF DESCRIPTION OF THE INVENTION

In one exemplary embodiment, a medical imaging system is provided. The medical imaging system includes a gantry, a patient display, and a computer. The gantry at least partially circumscribes a patient viewing area. The patient display is viewable from the patient viewing area. The patient display is communicatively coupled to the computer. The computer is programmed to receive scan protocol instructions and control the patient display according to the predetermined scan protocol. It is further programmed to prompt the patient, using the patient display, to perform a bodily action that facilitates the scan and to provide the patient with at least one of entertainment and distraction using the patient display.

In another exemplary embodiment, a method of scanning a patient using a medical imaging device is provided. The method includes positioning the patient display within the field of view of the patient. The method further includes controlling the patient display according to the predetermined scan protocol and prompting the patient by making use of the patient display, to perform a bodily action that facilitates the scan. The method also includes providing the patient with at least one of entertainment and distraction by using the patient display. The method further includes generating an image of the patient from data acquired during the scan.

In another exemplary embodiment, a computer system including a software code segment is provided. The software code segment is programmed to control a medical imaging device to receive the predetermined scan protocol instructions. The software code segment is further programmed to control the patient display according to the predetermined scan protocol, to prompt the patient by using the patient display, to perform a bodily action that facilitates the scan and to provide the patient with at least one of entertainment and distraction using the patient display.

DETAILED DESCRIPTION OF THE INVENTION

Various embodiments of the invention provide a system, method and software code segment for providing a patient display to be viewed by patients during scanning. A patient display is provided to prompt a patient to regulate the patient's actions, for example, to prompt the patient to regulate his/her breathing. In addition the patient display acts as a distraction and provides entertainment to the patient. This helps to relieve the patient of anxiety and agitation, therefore, pacifying the patient.

Figure 1:
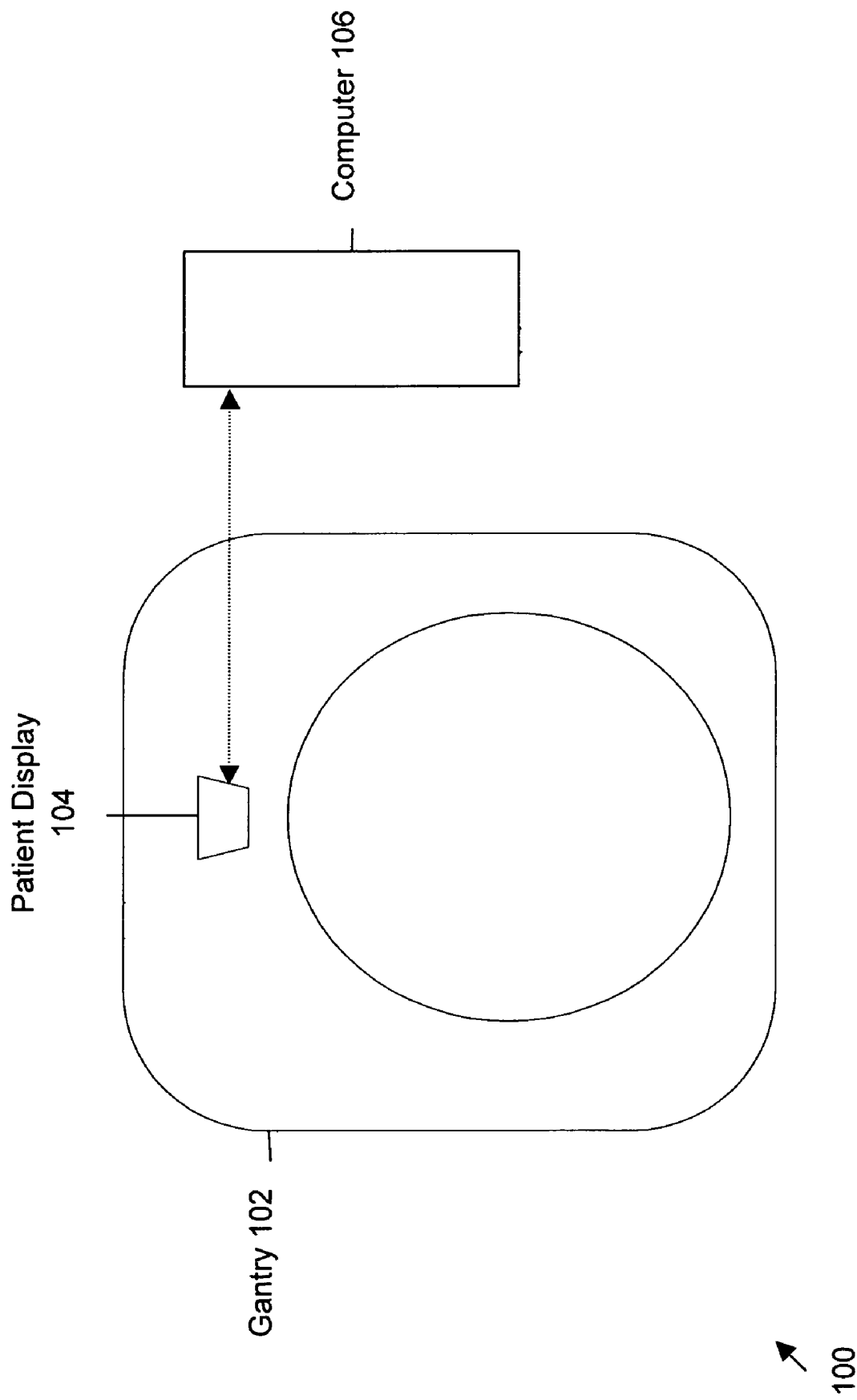
FIG. 1 is a block diagram of a medical imaging system in accordance with an exemplary embodiment of the invention.

FIG. 1 is a block diagram of a medical imaging system in accordance with an exemplary embodiment of the invention. A medical imaging system 100, for example a Computer Tomography (CT) system, is used to scan a patient and obtain an image of the patient. Medical imaging system 100 includes a gantry 102. Gantry 102 at least partially circumscribes a patient viewing area. Gantry 102 provides mechanical support for mounting devices, such as detectors, scanners and transmitters, which are required to scan the patient.

Medical imaging system 100 further includes a patient display 104. Patient display 104 is visible to a patient, even while he/she is being scanned. Patient display 104 can be a display of different types, such as a Thin Film Transistor Liquid Crystal Display (TFT LCD) capable of displaying full-motion video. In accordance to various embodiments of the invention, patient display 104 may be mounted on or coupled to gantry 102 or it may be positioned on a movable display stand and placed in proximity of gantry 102. Patient display 104 may be attached to gantry 102 in various ways, such as it may be mechanically fastened or magnetically coupled to gantry 102.

The matter displayed on patient display 104 is controlled by a computer system 106. Communication is enabled between computer system 106 and patient display 104. Computer system 106 controls the displayed matter based on a predetermined scan protocol that is fed into computer system 106. Computer system 106 is programmed to receive the predetermined scan protocol instructions. Computer system 106 is, further, programmed to control patient display 104 based on the predetermined scan protocol. The predetermined scan protocol provides an indication, of when and what is required for the patient to do, based on the scanning procedure. The control on the displayed matter may also be based on demographic data and preferences of the patient, as input to computer system 106. Based on the scan protocol and the demographic data of the patient, computer system 106 may automatically select the matter to be displayed. This display is in accordance with a predetermined display script, such as a prerecorded audio and/or visual clip. In accordance with various embodiments of the invention, patient display 104 can be controlled based on responses from the patient. For this purpose, medical imaging system 100 may receive patient response, such as an audio response.

In accordance with various embodiments of the invention, the matter displayed provides the patient entertainment. This distracts the patient from the actual scanning procedure. The entertainment and distraction relieves the patient of any anxiety that the patient might be experiencing. In addition, this pacifies the patient when the patient is agitated.

Patient display 104 may also be used to prompt the patient to perform a bodily action, such as, it may prompt the patient to hold his/her breath. The promptings may be in an audio or visual form or as a combination of the two. Computer system 106 may, therefore, be programmed to issue pre-recorded verbal commands to the patient. These verbal commands, in accordance with various embodiments of the invention may be issued in the patient's native language, or in his/her choice of language.

In accordance with various embodiments of the invention, visual prompts may be in various forms such as text, graphics or a combination of the two. The displayed text may be in the patient's language of choice or native language. Further, the displayed graphics may include international symbols to prompt the patient, indicating to him/her what is to be done. The graphics may include pre-recorded videos, moving images, animations or a combination of the same.

Figure 2:
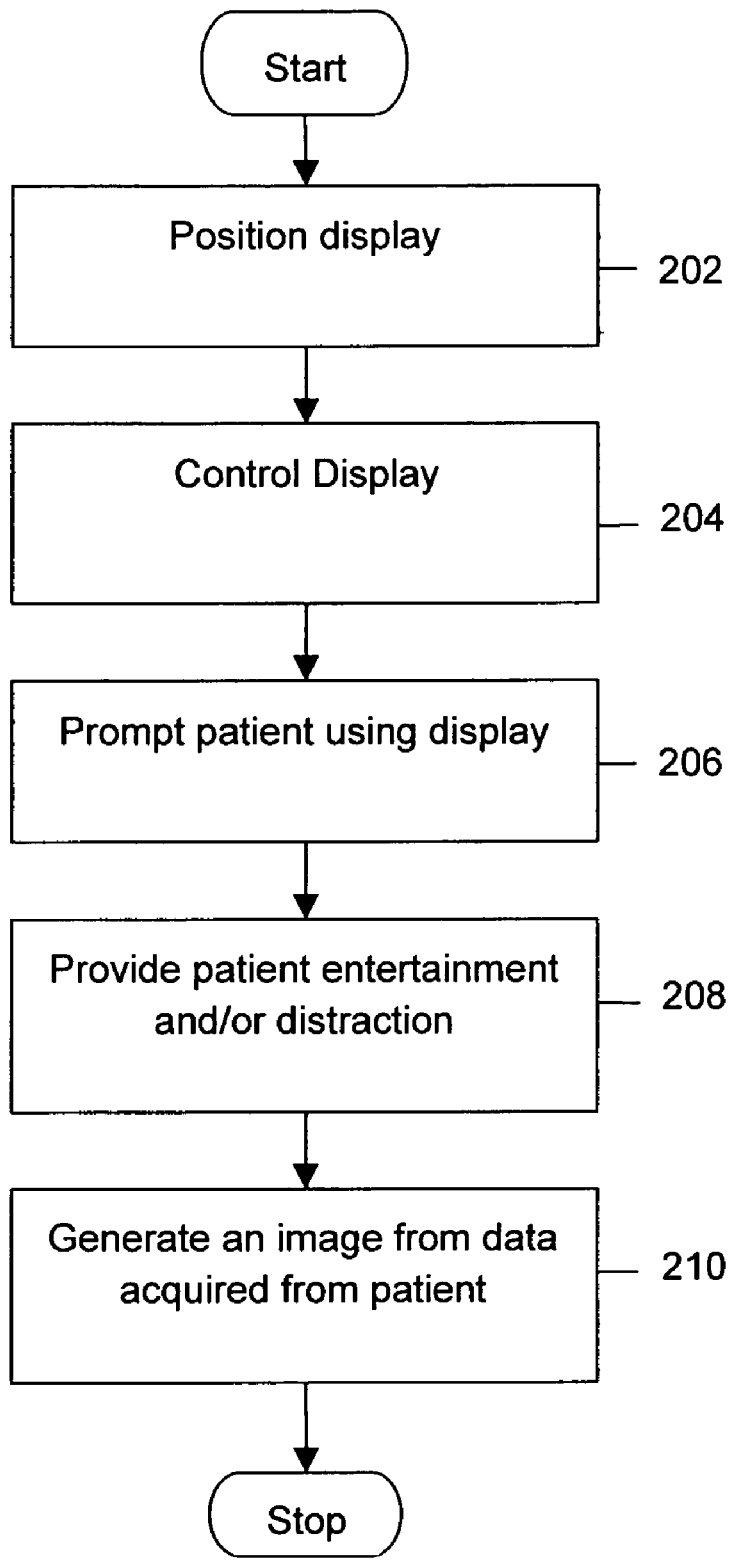
FIG. 2 is a flowchart for showing the steps for scanning a patient, in accordance with various embodiments of the invention.

The method of scanning the patient making use of medical imaging system 100 is described in detail in the following description. FIG. 2 is a flowchart showing the steps for scanning a patient, in accordance with various embodiments of the invention. The patient is scanned while performing the following steps. At 202, patient display 104 is positioned within the field of view of the patient to be scanned. Patient display 104 is positioned is such a way that it is visible to the patient, without any difficulty, throughout the process of scanning. This positioning may include coupling patient display 104 to gantry 102, as described earlier. The positioning may also be performed by adjusting and positioning the movable display stand, in proximity of gantry 102, in case it holds patient display 104.

At 204, patient display 104 is controlled in accordance with a predetermined scan protocol. The predetermined scan protocol may, for example, determine when the patient should breathe in or breathe out or hold his/her breath. The scan protocol determines the actions to be performed by the patient based on the scanning procedure that is being performed. The predetermined scan protocol is stored in computer system 106. Therefore, based on the predetermined scan protocol, computer system 106 controls patient display 104.

At 206, the patient is prompted to perform a bodily action that facilitates the scan, by using patient display 104. This prompted bodily action may be, for example, normal breathing, holding one's breath, taking deep breaths, filling of one's lungs to a particular threshold, and lying steady. This bodily action is prompted based on the scan protocol and is of significance to the success of the scan. For example, for CT scans it may be required that the patient regulates his/her breathing rate and level. Patients can regulate their breathing patterns by performing the bodily actions as prompted by patient display 104. These promptings, as described earlier, may be in the form of text, graphics and sound.

At 208, patient display 104 provides the patient entertainment and/or distraction from the actual procedure of scanning. This may be done, for example, by displaying various graphics, sounds or text. As described earlier, the entertainment and distraction pacifies the patient when the patient is agitated. The method of controlling patient display 104, for entertainment and/or distraction and for providing the prompts, is described further with reference to FIG. 3.

At 210, an image is generated of the patient based on the data that is acquired during the performed scan. The various devices supported on gantry 102, such as detectors and scanners acquire this data for generating the image.

Figure 3:
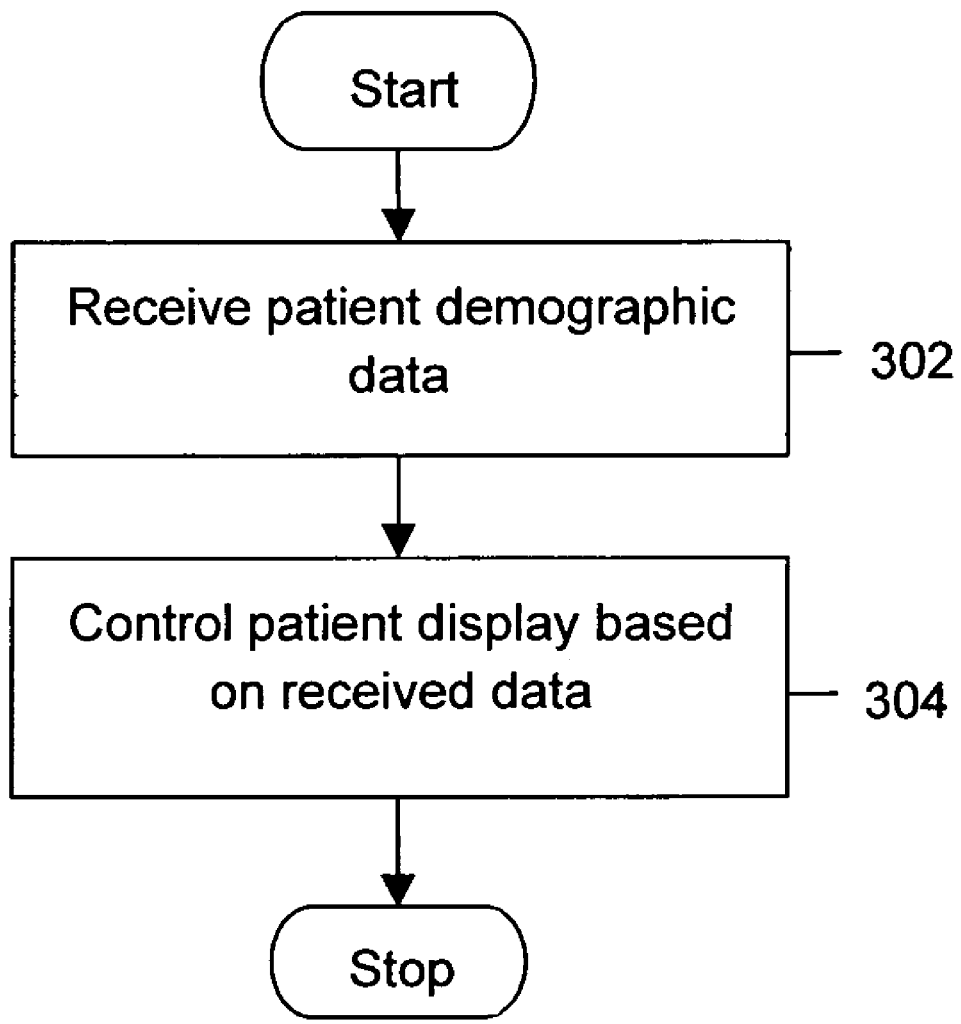
FIG. 3 is a flowchart showing the steps involved in controlling the patient display, in accordance with an exemplary embodiment of the invention.

FIG. 3 is a flowchart for showing the steps involved in controlling patient display 104, in accordance with various exemplary embodiments of the invention. At 302, demographic data of the patient is received by computer system 106. This demographic data may include details about the patient, such as the patient's native language, the chronological age of the patient, an approximate mental age of the patient and the gender of the patient. The received data may also include details about the entertainment preferences of the patient, such as choice of type of language, music or interests and hobbies. Various other details, in order to customize the displayed matter may also be received, for example if animations or cartoons are to be displayed, the received data may also include details about the patient's favorite cartoon character, and so on.

At 304, patient display 104 is controlled based on the received demographic data. Computer system 106, as described earlier, selects a predetermined script based on the received demographic data and the predetermined scan protocol. The demographic data is used in order to customize the displayed matter. The display is customized and the predetermined script is selected such that the patient finds it to his/her liking and is easy for the patient to comprehend and follow. For example, for a child of four his/her favorite cartoon characters may be displayed, while, for a sport enthusiast, an animation of his/her favorite sportsperson may be displayed.

The presentation of the prompts to be given to the patient may also be customized based on the received demographic data. Taking the previous example, if the four year old is to be prompted to hold his/her breath, the child may be shown his favorite cartoon character doing the same and prompting the child to follow the actions. In case the sport enthusiast is to be told the same, a verbal prompt in the voice of his/her favorite sportsperson may be played.

In accordance with various embodiments of the invention, the promptings are based on the actions of the patient. The patient's actions are monitored. Based on these monitored actions, the prompts are provided to the patient as a feedback. For this purpose, medical imaging system senses the actions of the patient. For example, it senses if the patient is breathing in or holding his/her breath. Based on this information, it provides a feedback to the patient by prompting the patient to do what is expected from the patient.

Figure 4:
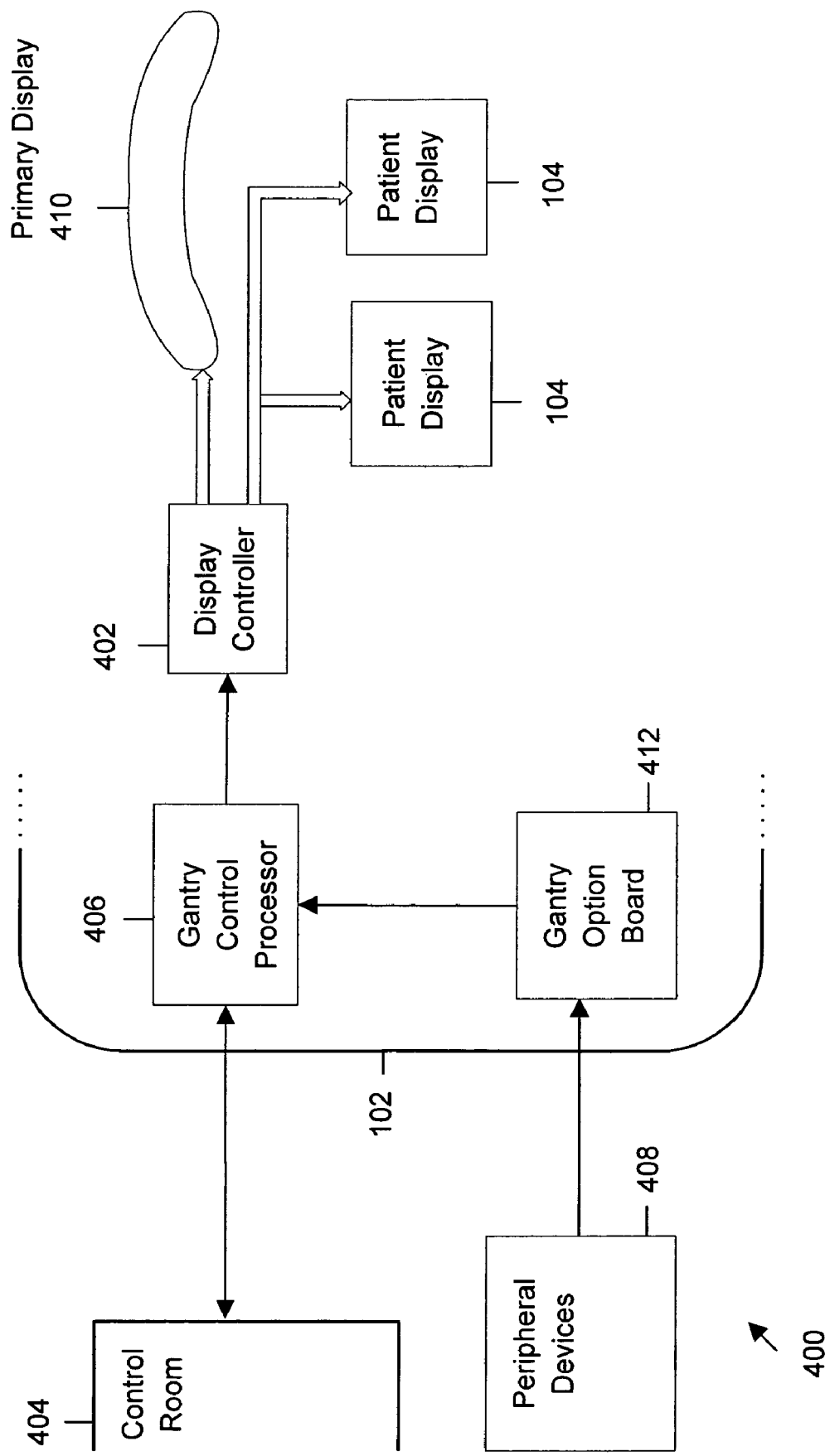
FIG. 4 is a block diagram of an exemplary medical imaging system employing feedback.

FIG. 4 is a block diagram of an exemplary medical imaging system employing feedback. In accordance with various embodiments of the invention, a medical imaging system 400 may include patient display 104 on the front and rear faces of gantry 102. Patient display 104 is controlled by various devices within computer system 106 as described hereinafter.

Patient display 104 is controlled by a display controller 402. This control is based on the information that is communicated from a control room 404. The information reaches display controller 402 via a gantry control processor 406.

Control room 404 sends out information based on data received from various peripheral devices 408. Medical imaging system 400 also includes a primary display 410 that gives instructions and feedback to a technician.

Information from control room 404 is communicated to gantry 102. Gantry control processor 406 then interprets the information. It further sends control commands based on the interpreted information. These control commands are sent to display controller 402. Display controlled 402 converts the control commands into renderings. These renderings are then forwarded to patient display 104. Patient display 104 displays the renderings to the patient. The renderings vary depending on the activities needed for scanning. The selection of renderings is made based on the control and configuration data sent from control room 404.

In addition, in accordance with various embodiments of the invention, peripheral devices 408 may be connected to medical imaging system 400. Peripheral devices 408, for example respiration monitors, monitor various actions of the patient. For example, peripheral devices 408 may monitor the breathing or heart rate of the patient. Peripheral devices 408 send data based on these actions of the patient to a gantry option board 412. Gantry option board 412 converts this data into control data. Gantry control processor 406 processes such peripheral control data. This permits display controller 402 to respond to the input of peripheral devices 408, and modifying the renderings accordingly. Patient display 104 can, therefore, be modified according to the data from peripheral devices 408. This means that patient display is controlled by the actions of the patient, and patient display in turn provides a feedback to the patient.

Various embodiments of the invention provide a noninvasive system and method to pacify patients during scanning.

Various embodiments of the invention provide a system and method to customize a patient display according to the demographic data and preferences of the patient.

Various embodiments of the invention provide a system and method to entertain and distract the patients from the scanning procedure. The entertainment and distraction reduces the anxiety and nervousness of the patient and improves the experience of the patient.

A technical effect of various embodiments of the invention is reducing movement artifacts. Movement artifacts are reduced by reducing fidgeting and movement of the patient. This is achieved by prompting the patient to keep still in a way he/she can comprehend and is willing to follow. This can also be achieved by entertaining and distracting the patient, thereby, reducing the patient's uneasiness and anxiety.

The various embodiments or components thereof may be implemented as part of computer system 106. Computer system 106 may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into computer system 106.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

Computer system 106 executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A method of scanning a patient using a medical imaging device, said method comprising:
receiving patient demographic data comprising an approximate mental age of the patient, wherein the approximate mental age of the patient is different than the intelligence quotient of the patient;
positioning a display within a field of view of the patient;
controlling the display according to a predetermined scan protocol and the received patient demographic data;
selecting a display script based on the received patient demographic data and the scan protocol;
prompting the patient, using the display script, to perform a bodily action that facilitates a scan, the patient prompted by receiving instructions indicative of the bodily action;
providing the patient with at least one of entertainment and distraction using the display script; and
generating an image of the patient from data acquired during the scan.

2. A method in accordance with claim 1 wherein positioning a display within a field of view of the patient comprises at least one of coupling the display to a medical imaging device gantry and positioning a movable display stand proximate the gantry.

3. A method in accordance with claim 2 wherein coupling the display to a medical imaging device gantry comprises at least one of magnetically coupling the display to the medical imaging device gantry and mechanically fastening the display to the medical imaging device gantry.

4. A method in accordance with claim 1 wherein providing the patient with at least one of entertainment and distraction using the display comprises providing the patient with at least one of entertainment and distraction during periods of patient agitation.

5. A method in accordance with claim 1 wherein receiving patient demographic data comprises receiving at least one of a native language of the patient, a chronological age of the patient, an entertainment preference of the patient, and a gender of the patient.

6. A method in accordance with claim 1 wherein prompting the patient to perform a bodily action that facilitates the scan using the display comprises prompting the patient to perform a bodily action using at least one of text, sound, and graphics through the display.

7. A method in accordance with claim 6 wherein prompting the patient to perform a bodily action using graphics comprises displaying the prompted bodily action using international symbols.

8. A method in accordance with claim 6 wherein prompting the patient to perform a bodily action using graphics comprises displaying the prompted bodily action using moving images.

9. A method in accordance with claim 8 wherein displaying the prompted bodily action using moving images comprises displaying the prompted bodily action using pre-recorded video.

10. A method in accordance with claim 8 wherein displaying the prompted bodily action using moving images comprises displaying the prompted bodily action using animation.

11. A method in accordance with claim 6 wherein prompting the patient to perform a bodily action using sound comprises issuing pre-recorded verbal commands to the patient.

12. A method in accordance with claim 11 wherein issuing pre-recorded verbal commands to the patient comprises issuing pre-recorded verbal commands to the patient in the patient's language of choice.

13. A method in accordance with claim 6 wherein prompting the patient to perform a bodily action using text comprises displaying textual commands to the patient in the patient's language of choice.

14. A method in accordance with claim 1 further comprising receiving an audio response from the patient.

15. A method in accordance with claim 14 further comprising providing the patient with at least one of entertainment and distraction during the scan using the audio response.

16. A method in accordance with claim 1 wherein prompting the patient to perform a bodily action that facilitates the scan using the display comprises:
    monitoring actions performed by the patient; and
    prompting the patient to perform bodily actions based on the monitored actions.

17. A medical imaging system comprising:
    a gantry at least partially circumscribing a patient viewing area;
    a patient display viewable from said patient viewing area; and
    a computer communicatively coupled to said patient display, said computer programmed to:
    receive patient demographic data comprising an approximate mental age of the patient, wherein the approximate mental age of the patient is different than the intelligence quotient of the patient;
    receive scan protocol instructions;
    control the patient display according to the scan protocol instructions and the received patient demographic data;
    select a display script based on the received patient demographic data and the scan protocol instructions;
    prompt the patient, using the display script, to perform a bodily action that facilitates a scan, the patient prompted by receiving instructions indicative of the bodily action; and
    provide the patient with at least one of entertainment and distraction using the display script.

18. A medical imaging system in accordance with claim 17 comprising a computed tomography scanner.

19. A medical imaging system in accordance with claim 17 wherein said display is at least one of coupled to the gantry and positioned on a movable display stand proximate the gantry.

20. A medical imaging system in accordance with claim 19 wherein said display is at least one of magnetically coupled to the gantry and mechanically fastened to the gantry.

21. A medical imaging system in accordance with claim 17 wherein said computer is further programmed to provide the patient with at least one of entertainment and distraction during periods of patient agitation using the patient display.

22. A medical imaging system in accordance with claim 17 wherein said computer is further programmed to receive at least one of a language of choice of the patient, a chronological age of the patient, an entertainment preference of the patient, and a gender of the patient.

23. A medical imaging system in accordance with claim 17 wherein said computer is further programmed to prompt the patient to perform a bodily action using at least one of text, sound, and graphics through the patient display.

24. A medical imaging system in accordance with claim 23 wherein said computer is further programmed to display the prompted bodily action using international symbols.

25. A medical imaging system in accordance with claim 23 wherein said computer is further programmed to display the prompted bodily action using moving images.

26. A medical imaging system in accordance with claim 25 wherein said computer is further programmed to display the prompted bodily action using at least one of pre-recorded video and animation.

27. A medical imaging system in accordance with claim 17 wherein said computer is further programmed to issue pre-recorded verbal commands to the patient.

28. A medical imaging system in accordance with claim 27 wherein said computer is further programmed to issue pre-recorded verbal commands to the patient in the patient's language of choice.

29. A medical imaging system in accordance with claim 23 wherein said computer is further programmed to display textual commands to the patient in the patient's language of choice.

30. A medical imaging system in accordance with claim 17 further comprising receiving an audio response from the patient.

31. A medical imaging system in accordance with claim 30 providing the patient with at least one of entertainment and distraction during the scan using the audio response.

32. A medical imaging system in accordance with claim 17 wherein said computer is further programmed to:
    monitor actions performed by the patient; and
    prompt the patient to perform bodily actions based on the monitored actions.

33. A computer system comprising a non-transitory memory having a software code segment stored thereon and programmed to control a medical imaging device to receive predetermined scan protocol instructions and then:

receive patient demographic data comprising an approximate mental age of the patient, wherein the approximate mental age of the patient is different than the intelligence quotient of the patient;

control a patient display according to the predetermined scan protocol instructions and the received patient demographic data;

select a display script based on the received patient demographic data and the scan protocol instructions;

prompt the patient, using the display script, to perform a bodily action that facilitates a scan, the patient prompted by receiving instructions indicative of the bodily action; and provide the patient with at least one of entertainment and distraction using the display script.

34. A computer system in accordance with claim 33 wherein said software product code segment is configured to control a computed tomography scanner.

35. A computer system in accordance with claim 33 wherein said display is at least one of magnetically coupled to the gantry, mechanically fastened to the gantry, and positioned on a movable display stand proximate the gantry.

36. A computer system in accordance with claim 33 wherein said computer is further programmed to provide the patient with at least one of entertainment and distraction during periods of patient agitation using the patient display.

37. A computer system in accordance with claim 33 wherein said computer is further programmed to receive at least one of a language of choice of the patient, a chronological age of the patient, an entertainment preference of the patient, and a gender of the patient.

38. A computer system in accordance with claim 33 wherein said computer is further programmed to prompt the patient to perform a bodily action using at least one of text, sound, and graphics through the patient display.

39. A computer system in accordance with claim 38 wherein said computer is further programmed to display the prompted bodily action using at least one of international symbols, moving images, pre-recorded video and animation.

40. A computer system in accordance with claim 33 wherein said computer is further programmed to issue pre-recorded verbal commands to the patient in the patient's language of choice.

41. A computer system in accordance with claim 38 wherein said computer is further programmed to prompt the patient to perform a bodily action using text in the patient's language of choice.

42. A computer system in accordance with claim 33 wherein said computer is further programmed to receive an audio response from the patient.

43. A computer system in accordance with claim 42 wherein said computer is further programmed to provide the patient with at least one of entertainment and distraction during the scan using the audio response.

44. A computer system in accordance with claim 33 wherein said computer is further programmed to:
monitor actions performed by the patient; and
prompt the patient to perform bodily actions based on the monitored actions.

* * * * *